United States Patent [19]
Henderson et al.

[11] Patent Number: 5,698,443
[45] Date of Patent: *Dec. 16, 1997

[54] TISSUE SPECIFIC VIRAL VECTORS

[75] Inventors: Daniel Robert Henderson, Palo Alto; Eric Rodolph Schuur, Cupertino, both of Calif.

[73] Assignee: Calydon, Inc., Menlo Park, Calif.

[*] Notice: The term of this patent shall not extend beyond the expiration date of Pat. No. 5,648,478.

[21] Appl. No.: 495,034

[22] Filed: Jun. 27, 1995

[51] Int. Cl.$^6$ .................... A61K 48/00; C12N 5/00; C12N 15/00

[52] U.S. Cl. .................... 435/320.1; 435/172.3; 435/240.1; 435/240.2; 435/252.3; 514/2; 514/44; 424/93.21

[58] Field of Search .................... 424/93.1, 93.21; 514/44; 435/240.1, 252.3, 320.1, 172.3; 536/23.1

[56] References Cited

FOREIGN PATENT DOCUMENTS 9428152  12/1994  WIPO.

OTHER PUBLICATIONS

Bett et al., "Packaging Capacity and Stability of Human Adenovirus Type 5 Vectors", J. of Virology (1993), 5911–5921.
Graham, "Covalently Closed Circles of Human Adenovirus DNA are Infectious", EMBO Journal (1984), 3:2917–2922.
Graham and Van der Eb, "A New Technique for the Assay of Infectivity of Human Adenovirus 5 DNA", Virology (1973), 52:456–467.
Berkner and Sharp, "Generation of Adenovirus by Transfection of Plasmids", Nucleic Acids Research (1983), 11:6003–6020.
Takiff et al., "Propagation and In Vitro Studies of Previously Non–Cultivable Enteral Adenoviruses in 293 Cells", The Lancet (1981), 832–834.
Bett et al., "An Efficient and Flexible System for Construction of Adenovirus Vectors with Insertions or Deletions in Early Regions 1 and 3", P.N.A.S. (1994), 91:8802–8806.
Marshall, Science, 269, 1995, 1050–1055.
Culver et al, TIG, 10(5), 1994, 174–178.
Hodgson, Exp. Opin. Ther. Pat., 5(5), 1995, 459–468.
Miller et al., FASEB Journal, 9, 1995, 190–199.
Gotoh et al., J. Urology, 153, 4 Supp., 1995, 308 A.
Taneja et al., Proc. Amer. Assoc. Can. Res., 35 (0), 1994, 375.
Ko et al., J. Cell. Biochem., Supp., O (21A), 1995.

Primary Examiner—Jacqueline M. Stone
Assistant Examiner—Andrew K. Milne

[57] ABSTRACT

Host cell specific adenovirus vehicles are provided for transfecting target host cells. By providing for transcriptional initiating regulation dependent upon transcription factors that are only active in specific, limited cell types, virus replication will be restricted to the target cells. The modified adenovirus may be used as a vehicle for introducing new genetic capability, particularly associated with cytotoxicity for treating neoplasia.

12 Claims, No Drawings

TISSUE SPECIFIC VIRAL VECTORS

TECHNICAL FIELD

The field of this invention is cell transfection.

BACKGROUND

For many medical applications, there is an interest in being able to specifically modify target cells in vivo or ex vivo. The modification can be associated with random DNA integration, whereby a genetic capability is introduced that complements a genetic defect intracellularly, provides for secretion of a product from the modified cells, which is otherwise indetectably produced or not produced by the host, provide protection from disease, particularly viral disease, and the like. In many situations, in order to be effective, one must have a high efficiency of transfection of the target cells. This is particularly true for in vivo modification. In addition, one would wish to have a high specificity for the target cells, as compared to other cells that may be present ex vivo or in vivo.

Gene therapy involves the transfer of cloned genes to target cells. A variety of viral and non-viral vehicles have been developed to transfer these genes. Of the viruses, retroviruses, herpes virus, adeno-associated virus, Sindbis virus, poxvirus and adenoviruses have been used for gene transfer. These vehicles all have different properties. For example, retroviruses transduce genes in vitro with high efficiency by integrating the transduced gene into the chromosome following division of infected cells. Adeno-associated viruses can stably integrate into and express transduced genes in both dividing and quiescent cells. In contrast, liposomes and adenovirus allow only transient gene expression, and transduce both dividing and quiescent target cells.

Of the viruses, adenoviruses are among the most easily produced and purified, whereas retroviruses are unstable, difficult to produce and impossible to purify. Both classes of virus transduce cells with high efficiency. Liposomes hold the promise of allowing repeat doses of genes for, unlike viruses, they are not immunogenetic. However, liposomes complexed with DNA are difficult to produce in commercial quantities, and are inefficient gene transfer vehicles, most often transducing fewer than one percent of target cells.

There are two major divisions of gene therapy protocols: in vivo and ex vivo. In vivo refers to administration of the therapeutic directly to the patient, usually by inhalation or injection, although oral administration has been suggested in some instances. Ex vivo gene therapy refers to the process of removing cells from a patient, for example in a biopsy, placing the cells into tissue culture, transferring genes to the cells in tissue culture, characterizing the newly genetically engineered cells, and finally returning the cells to the patient by intravenous infusion. Therapeutically, retroviruses are most often used for ex vivo transfer, whereas adenoviruses and liposomes are most often used for in vivo gene transfer.

In the treatment of cancer by replication defective adenoviruses, the host immune response limits the duration of repeat doses of the therapeutic at two levels. First, the adenovirus delivery vehicle itself is immunogenic. Second, late virus genes are frequently expressed in transduced cells, eliciting cellular immunity. Thus, the ability to repeatedly administer cytokines, tumor suppressor genes, ribozymes or suicide genes is limited by the transient nature of gene expression, as well as the immunogenicity of both the gene transfer vehicle and the viral gene products of the transfer vehicle.

The first case, the immunogenicity of the vector, is akin to the problem facing mouse monoclonal antibodies complexed with bacterial toxins that are directed against tumor-specific antigens. Use of these proteins as a therapeutic, popular a decade ago, failed due to the high doses required and ultimately, to immunogenicity. The same fate may befall replication defective adenoviruses, unless the efficacy can be improved to achieve clinical useful therapeutic endpoints before immunogenicity of a transfer vehicle limits repeat usage.

In the second case, steps have been taken to eliminate the unwanted transcription and expression of late adenovirus genes in transduced cells, with its resulting immunogenicity.

There is, therefore, substantial interest in being able to develop viral vectors which substantially reduce the present limitations and restrictions on the use of such vectors in vivo.

RELEVANT LITERATURE

Graham and Van de Eb (1973) *Virology* 52:456–467; Takiff et al. (1981) *Lancet* ii:832–834; Berkner and Sharp (1983) *Nucleic Acid Research* 11:6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806 describe adenoviruses that have been genetically modified to produce replication defective gene transfer vehicles. In these vehicles, the early adenovirus gene products E1A and E1B are deleted and provided in trans by the packaging cell line 293 developed by Frank Graham (Graham et al. (1987) *J. Gen. Virol.* 36:59–72 and Graham (1977) *J. General Virology* 68:937–940). The gene to be transduced is commonly inserted into adenovirus in the deleted E1A and E1B region of the virus genome Bett et al. (1994), supra. Adenovirus vectors as vehicles for efficient transduction of genes have been described by Stratford-Perricaudet (1990) *Human Gene Therapy* 1:241–256; Rosenfeld (1991) *Science* 252:431–434; Wang et al. (1991) *Adv. Exp. Med. Biol.* 309:61–66; Jaffe et al. (1992) *Nat. Gent.* 1:372–378; Quantin et al. (1992) *Proc. Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal Le Salle et al. (1993) *Science* 259:988–990; Mastrangeli et al. (1993) *J. Clin. Invest.* 91:225–234; Ragot et al. (1993) *Nature* 361:647–650; Hayaski et al. (1994) *J. Biol. Chem.* 269:23872–23875.

SUMMARY OF THE INVENTION

Adenovirus vectors, and methods for their use as vehicles for the transduction of restricted cell types, are provided. The adenovirus vectors are either replication defective or competetent. For replication defective adenovirus vectors, the adenoviruses can only be propagated in target cells in which early genes can be complemented in trans. Additionally, one or more late genes and/or one or more transgenes may be under the control of a transcriptional initiation region that is transcriptioanlly active only in the target cells of interest. For replication competent adenovirus vectors, one or more of the promoters of the early and/or late genes essential for propagation is replaced with the transcriptional initiation region described above, where a transgene under a cell specific promoter may also be present. The adenovirus vectors find use in the treatment of various indications and for making mammalian hosts that are transiently transgenic, and allowing for regulated adenovirus propagation and transgene expression, in parallel with the cellular regulation of the endogenous transcriptional initiation region.

DESCRIPTION OF THE SPECIFIC EMBODIMENTS

Replication defective or replication competent adenovirus vehicles are provided. The viruses comprise at least one gene under the transcriptional control of a transcriptional initiation region specifically regulated by target host cells. The genes that are regulated by the specifically regulated transcriptional initiation region may be early or late adenovirus genes and/or transgenes. By providing for regulated transcription restricted to specific host cell targets, one can provide for adenoviruses that can be used as vehicles for introducing genetic capability into host target cells, as distinct from other host cell types. The transgenes serve to modify the genotype or phenotype of the target cell, in addition to any modification of the genotype or phenotype resulting from the presence of the adenovirus.

There are a number of different types of adenovirus, such as Ad2, Ad5, and Ad40, which may differ to minor or significant degrees. Particularly, Ad5 and Ad40 differ as to their host cell tropism, as well as the nature of the disease induced by the virus. For the purpose of the subject invention, Ad5 will be exemplified.

The genes of the adenovirus that are of interest for the subject invention may be divided into two groups, the early genes and the late genes, the expression of the latter being controlled by the major late promoter. Of the early genes, there are E1A, E1B, E2, E3 and E4. The E1A gene is expressed immediately after viral infection (0–2 h) and before any other viral genes. E1A protein acts as a trans-acting, positive-acting transcriptional regulatory factor, and is required for the expression of the other early viral genes and the promoter proximal major late genes. Despite the nomenclature, the promoter proximal genes driven by the major late promoter are expressed during early times after Ad5 infection. In the absence of a functional E1A gene, viral infection does not proceed, because the gene products necessary for viral DNA replication are not produced.

The E1B protein functions in trans and is necessary for transport of late mRNA from the nucleus to the cytoplasm. Defects in E1B expression result in poor expression of late viral proteins and an inability to shut off host cell protein synthesis.

The E4 gene has a number of transcription products. Open reading frames (ORF) 3 and ORF6 of the E4 transcription unit increase the accumulation of major late transcription unit mRNAs by binding the 55-kDa protein from E1B and heterodimers of E2F-1 and DP-1. In the absence of functional protein from ORF3 and ORF6, plaques are produced with an efficiency less than $10^{-6}$ of that of wild type virus.

The major late genes relevant to the subject invention are genes such as L1, L2 and L3, which encode proteins of the AD5 virus virion.

The subject vectors can be used for a wide variety of purposes. The purpose will vary with the target cell. Suitable target cells are characterized by the transcriptional activation of the cell specific transcriptional response element in the adenovirus vehicle. The transcription initiation region will usually be activated in less than about 5%, more usually less than about 1%, and desirably by less than about 0.1% of the cells in the host.

Regulation of transcriptional activation is the result of interaction between transcriptional activators bound to cis-regulatory elements, factors bound to basal transcriptional elements and the activity of transcriptional mediators, or coactivators. The absence or presence of any of these factors may affect the level of transcription. Additionally, factors may be present in an inactive form, where the factors are activated through chemical modification, particularly as the result of a cellular signaling mechanism. In some cases, signaling molecules are able to act directly to activate transcription. Any of these mechanisms may operate to limit the types of cells in which the vehicle transcription initiation region is active.

It will be understood by one of skill in the art that very low basal levels of transcription may be present in non-targeted cell types. By transcriptional activation, it is intended that trancription will be increased above basal levels in the target cell by at least about 100 fold, more usually by at least about 1000 fold.

The cell specific response element may be used with an adenovirus gene that is essential for propagation, so that replication competence is only achievable in the target cell, and/or with a transgene for changing the phenotype of the target cell. By transgene is intended any gene that is not present in wild-type adenovirus, frequently the transgene will also not be expressed in the target cell, prior to introduction by the adenovirus.

As exemplified by employing a cell specific response element comprising a promoter and enhancer construct specific for prostate cells, various genetic capabilities may be introduced into prostate cells expressing prostate specific antigen. Of particular interest is the opportunity to introduce cytotoxic effects that are controlled by a transcriptional initiation region specifically active in prostate cells. Other cell types that have specific active transcription factors associated with a state for which modulation is desirable include leukocytes, particularly lymphocytes, epithelial cells, endothelial cells, hepatic cells, pancreatic cells, neuronal cells and keratinocytes. Since the adenovirus results in transient expression (approximately 6 to 8 weeks), one can provide transient capability to cells, where the desired result only requires a limited period for response.

Purposes for intoducing transient expression include indications that may be treated involving undesired proliferation other than tumors, such as psoriatic lesions, restenosis, wound healing, tissue repair, enhanced immune response, resistance to infection, production of factors, enhanced proliferation, etc. By identifying genes that are expressed specifically by the target host cells, based on the nature of the cells, their level of maturity or their condition, the target cell specific response element can be used to provide genetic capability to such cells, where the genetic capability will be absent in other cells, even when transfected with the adenovirus vehicle.

The region that is employed to provide cell specificity dependent upon androgens, particular in prostate cells, involves an approximately 1.5 kb enhancer region and a 0.5 kb promoter region. The enhancer region in humans is located between nt −5322 and nt −3739, relative to the transcription start site of the prostate specific antigen (PSA) gene. The promoter consists of nt −540 to nt +12. Juxtaposition of the two genetic elements yields a fully functional, minimal prostate-specific enhancer/promoter (PSE). The enhancer contains three regions that bind prostate-specific DNA binding proteins, one of which contains a putative androgen response element. The promoter region contains typical TATA and CAAT boxes as well as a second putative androgen response element.

The vectors are conveniently prepared by employing two plasmids, one plasmid providing for the left hand region of adenovirus and the other plasmid providing for the right hand region, where the two plasmids share at least about 500 nt of middle region for homologous combination. In this way, each plasmid, as desired, may be independently manipulated, followed by cotransfection in a competent host, providing complementing genes as appropriate, or the appropriate transcription factors for initiation of transcription from the PSE for propagation of the adenovirus.

For convenience, plasmids are available that provide the necessary portions of the adenovirus. Plasmid pXC.1 (McKinnon (1982) *Gene* 19:33–42) contains the wild-type left-hand end of Ad5. pBHG10 (see Bett et al., supra) provides the right-hand end of Ad5, with a deletion in E3. The deletion in E3 provides room in the virus to insert the 2 kb minimal PSE without deleting the wild-type enhancer-promoter. The gene for E3 is located on the opposite strand from E4 (r-strain).

For manipulation of the early genes, the transcription start site of Ad5 E1A is at nt 560 and the ATG start site of the E1A protein is at nt 610 in the virus genome. This region can be used for insertion of the cell specific element, e.g. PSE. Conveniently, a restriction site may be introduced by employing the polymerase chain reaction (PCR), where the primer that is employed may be limited to the Ad5 genome, or may involve a portion of the plasmid carrying the Ad5 genomic DNA. For example, where pBR322 is the backbone, the primers may use the EcoRI site in the pBR322 backbone and the XbaI site at nt 1339 of Ad5. By carrying out the PCR in two steps, where overlapping primers at the center of the region introduce a sequence change resulting in a unique restriction site, one can provide for insertion of the cell specific response element at that site.

A similar strategy may also be used for insertion of the cell specific response element to regulate E1B. The E1B promoter of Ad5 consists of a single high-affinity recognition site for Sp1 and a TATA box. This region extends from 1636 to 1701 nt. By insertion of the cell specific response element in this region, one can provide for cell specific transcription of the E1B gene. By employing the left-hand region modified with the cell specific response element regulating E1A, as the template for introducing the cell specific response element to regulate E1B, the resulting adenovirus will be dependent upon the cell specific transcription factors for expression of both E1A and E1B.

For E4, one must use the right hand portion of the adenovirus genome. The E4 transcription start site is predominently at nt 35605, the TATA box at nt 35631 and the first AUG/CUG of ORF1 is at nt 35532 (Virtanen et al. (1984) *J. Virol.* 51: 822–831). Using any of the above strategies for the other genes, the cell specific response element may be introduced in this region between the transcription start site and the initiation codon. Once again, by employing a previously manipulated adenovirus genome, one can provide for a plurality of genes being dependent upon the target cell specific transcription factors, insuring that the adenovirus will be incapable of replication in cells lacking these transcription factors.

For replication defective viruses, one need only inactivate one or more of the genes essential for replication, carrying out the modifications of the genome in appropriate host cells which can complement the defect, so as to provide propagation of the replication defective viruses.

Genetic capability that may be introduced into the adenovirus vehicle includes a factor capable of initiating apoptosis, antisense or ribozymes, which among other capabilities may be directed to mRNAs encoding proteins essential for proliferation, such as structural proteins, transcription factors, polymerases, etc., viral or other pathogenic proteins, where the pathogen proliferates intracellularly, cytotoxic proteins, e.g. the α chains of diphtheria, ricin, abrin, etc., genes that encode an engineered cytoplasmic variant of a nuclease (e.g. RNase A) or protease (e.g. trypsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFNα, -β, -γ, TNFα, -β, TGFa, -β, NGF, and the like.

Other opportunities for specific genetic modification include T cells, such as tumor infiltrating lymphocytes (TILs), where the TILs may be modified to enhance expansion, enhance cytotoxicity, reduce response to proliferation inhibitors, enhance expression of lymphokines, etc. One may also wish to enhance target cell vulnerability by providing for expression of specific surface membrane proteins, e.g. B7, SV40 T antigen mutants, etc.

The modified viruses may be delivered to the target cell in a variety of ways, depending upon whether the cells are in culture, ex vivo or in vivo. For the prostate, for the most part, the cells will be delivered in vivo. Delivery can be achieved in a variety of ways, employing liposomes, direct injection, catheters, intravenous, inhalation, topical applications, etc. Due to the high efficiency of transfection of adenoviruses, one can achieve a high level of modified cells. In the case of neoplasia, where toxins are produced, the toxins will be released locally, so as to affect cells which may not have been successfully transfected. In this manner, one can specifically eliminate the neoplastic cells, without significant effect on the normal cells. In addition, expression of adenovirus proteins will serve to activate the immune system against the target cells. The adenovirus may be administered in an appropriate physiologically acceptable carrier at a dose of about $10^4$ to $10^{11}$. The multiplicity of infection will generally be in the range of about 0.001 to 100. The viruses may be administered one or more times, depending upon the immune response potential of the host. If necessary, the immune response may be diminished by employing a variety of immunosuppressants, so as to permit repetitive administration, without a strong immune response.

The following examples are offered by way of illustration and not by way of limitation.

EXPERIMENTAL

1. Prostate-specific enhancer/promoter (PSE)

The PSE enhancer region is located between nt −5322 and nt −3739 relative to the transcription start site of the prostate specific antigen gene. The promoter consist of nt −540 to nt +8. Juxtaposition of these two genetic elements yield to a fully functional minimal PSE.

The following is a diagram of the minimal PSE.

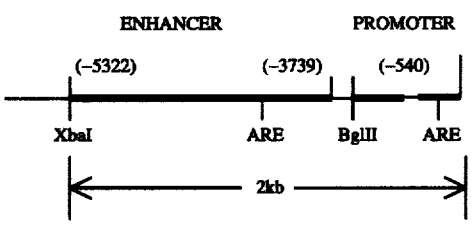

2. Complementary Host Cells pXE.1 is introduced into LNCaP cells by the method of Graham with slight modifications (Graham et al. (1977) *J.*

*Gen. Virol.* 36:59–72). The cells, patterned after 293 cells, are selected for production of high levels of E1A and E1B and designated CALY1. Following the above procedure, LNCaP cells are modified to express high levels of E4 using pBHG10, patterned after W162 cells (Weinberg and Ketner (1983) *Proc. Natl. Acad. Sci. USA* 80:5383–5386) and designated CALY2.

3. Adenovirus5 with PSE driving E1A gene

To insert the 2 kb minimal PSE into pXC.1, an AgeI site, ACCGGT, is introduced in the Ad5 genome at nt 598, 12 bp before the start codon of E1A. A linked PCR procedure is employed between the single EcoRI in the pBR322 backbone of pXC.1 and the single XbaI site at nt 1339 of Ad5. The following four primers are prepared:

1. [SEQ ID NO:1] 5' TCGTCTTCAA GAATTCTCA containing an EcoRI site within the pBR322 background 2. [SEQ ID NO:2] 5' GCATTCTCTA GACACAGGTG containing an XbaI site 3. [SEQ ID NO:3] 5' TCCGACACCG GTGACTGAAA containing an extra T to introduce an AgeI site 4. [SEQ ID NO:4] 5' TTTCAGTCAC CGGTGTCGGA containing an extra A to introduce an AgeI site Primers 1 and 4 are combined using pXC.1 as template, and primers 2 and 3 are combined again using pXC.1 as template and the PCR performed in accordance with the manufacturer's recommendations. Small aliquots of the PCR products are combined in a new PCR reaction using oligos 1 and 2 as primers. This results in a 1.7 kb (1714 bp) PCR product that is cut by AgeI into fragments of 927 bp and 787 bp. This plasmid is designated pCN95.

The minimal PSE is prepared by PCR with AgeI ends. The following primer oligos are prepared.

| [SEQ ID NO: 5] | 5' TAACCGGTACCTCTAGAAAATCTAGC AgeI       PSE |
|---|---|
|  |        KpnI |
| [SEQ ID NO: 6] | 5' TAACCGGTAAGCTTGGGGCTGGGG AgeI       PSE |

These two oligos are used in a PCR reaction with pCN65, minimal PSE driving a CAT reporter gene in BSKSII(+), as template. The PCR product with AgeI ends is cloned into the single AgeI site within pCN95 to produce pCN96 employing standard cloning procedures. (see Sambrook et al., *Molecular Cloning: A Laboratory Manual*, Cold Spring Harbor, N.Y., 1988). pCN96 is co-transfected with pBHG10 (see Bett et al., supra) into CALY2 cells, resulting in a replication defective prostate-specific virus designated Ad5RD: PSE/E1A:0 (Ad5 replication defective with driving E1A, without a transgene).

4. PSE driving E1B

The E1B promoter of Ad5 consists of a single high-affinity recognition site for Sp1 and a TATA box. An EagI site, CGGCCG, is created at Ad5 nt 1682 by inserting a G residue in pXC.1. Using PCR, the PSE is provided with EagI ends and cloned into the derivative of pXC.1 to give E1B driven by the minimal PSE (pCN100). pCN96 is also prepared with an EagI site in the promoter of E1B. Cloning in the PSE into this plasmid gives a construct where PSE drives both E1A and E1B (pCN105).

The following primers are employed to introduce an EagI site in the E1B promoter 1. [SEQ ID NO:7] 5' 5'TCGTCTTCAA GAATTCTCA containing an EcoRI site 2. [SEQ ID NO:8] 5' GCATTCTCTA GACACAGGTG containing an XbaI site 3. [SEQ ID NO:9] 5' GTATATAATG CGGCCGTGGG C containing an extra G to introduce an EagI site 4. [SEQ ID NO:10] 5' GCCCACGGCC GCATTATATA C containing an extra C to introduce an EagI site 5. PSE driving E4 pBHG10 is digested with EcoRI, and the 5 kb fragment from 30049 through 35935 as well as the first 188 nt of the left-hand end of the Ad5 genome are isolated. This 5 kb EcoRI fragment is cloned into pUC19. The E4 transcription start site is predominately at nt 35605, the TATA box at nt 35631 and the first AUG/CUG of ORF1 is at nt 35532. To insert the PSE for transcriptional control of E4, an analogous strategy is used as that for producing the AgeI site in the E1B promoter. A single XhoI site, CTCGAG, is created in the E4 enhancer/promoter at nt 35575. The PSE is cloned as a blunt PCR product into E4 at the XhoI site. The EcoRI fragment is now 7 kb, containing the 2 kb PSE, and is inserted into pBHG10 (pCN110). pCN110 is cotransfected with pΔE1Sp1A (see Bett et al., supra), with or without a PSE driven transgene in CALY1 cells to produce a PSE driven E4 Ad5 designated Ad5RD: PSE/E4: PSE transgene, and Ad5RD: PSE/E4: 0, respectively.

The following are the primer sequences used to introduce these XhoI site in the E4 promoter region.

1. [SEQ ID NO:11] 5' TAACTCACGT TGTGCATTGT containing a DraIII site at Ad5 nt 35142

2. [SEQ ID NO:12] 5' TCGTCTTCAAGAATTCTCA containing an EcoR1 site within the pBR322 background 3. [SEQ ID NO:13] 5' ACACCACTCG AGCACGGCAC C containing an extra G to introduce an Xho site 4. [SEQ ID NO:14] 5' GGTGCCGTGC TCGAGTGGTG A containing an extra C to introduce an Xho site 6. Preparation of the viruses Viruses are prepared by cotransfection of the two plasmids comprising the left hand and right hand portions of the Ad5, as described in Bett et el., supra. The plasmids are transfected into 293 cells by CaCl$_2$ precipitation (Graham and Van der Eb (1973) *Virology* 52:456–467; Graham (1984) *EMBO J.* 3:2917–2922). Viruses are twice banded in CsCl$_2$ and used for further experiments.

For preparing recombinant Ad5: PSE/E1A, pCN96 and pBHG10 are combined by homologous recombination. Ad5: PSE/E1B is prepared by homologous recombination of pCN100 and pBHG10. Ad5: PSE/E1A.E1B is prepared by homologous recombination of pCN105 and pBHG10.

Ad5: PSE/E1A.E4, Ad5: PSE/E1B.E4 and Ad5: PSE/E1A.E1B.E4 are prepared by homologous recombination with pCN110 and pCN96, pCN100 and pCN105, respectively, in LNCaP cells.

It is evident from the above results that adenoviruses can be provided as vehicles specific for particular host cells, where the viruses may be replication defective or replication competent. The viruses may be vehicles for a wide variety of genes for introduction in the target host cells. Particularly, employing the prostate specific element, the early genes essential for replication may be modified so as to be under the control of prostate cell responsive elements.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An adenovirus vector comprising an adenovirus early gene essential for propagation under the transcriptional control of a prostate cell specific response element for transcription of prostate specific antigen comprising an enhancer and promoter specific for a prostate cell.

2. An adenovirus vector according to claim 1, wherein said prostate cell specific response element comprises the enhancer sequence in the region −5322 to −3739 relative to the transcription start site of the prostate specific antigen gene.

3. An adenovirus vector according to claim 1 comprising transgene under the transcriptional control of said mammalian target cell response element.

4. An adenovirus vector according to claim 3, wherein said transgene is a cytotoxic gene.

5. An adenovirus vector comprising at least one of the genes E1A, E1B, or E4 under the transcriptional control of a prostate cell specific response element.

6. An adenovirus vector according to claim 5, wherein said adenovirus vector comprises a transgene under the transcriptional control of a prostate cell specific response element.

7. An adenovirus vector comprising a transgene under the transcriptional control of a prostate cell specific response element and lacking at least one of E1A, E1B, or E4 as a functional gene.

8. An adenovirus vector which is replication competent only in mammalian cells expressing prostate specific antigen.

9. An adenovirus vector according to claim 8, wherein at least one of the genes selected from the group consisting of E1A, E1B and E4 is under the transcriptional control of a prostate cell specific response element.

10. An adenovirus vector according to claim 8 comprising the transcriptional regulatory region enhancer of the human prostate specific antigen coming within nt −5322 to nt −3739 of the 5' non-coding region of the human prostate specific antigen, the numbering relative to the transcription start site of the human prostate specific antigen.

11. An adenovirus vector according to claim 8, wherein said adenovirus vector is Ad5.

12. A method for propagating an adenovirus specific for mammalian cells expressing prostate specific antigen, said method comprising:

combining an adenovirus according to claim 8 with mammalian cells expressing prostate specific antigen, whereby said adenovirus is propagated.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TCGTCTTCAA GAATTCTCA　　　　　　　　　　　　　　　　　　　　　　　　　　　　19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GCATTCTCTA GACACAGGTG　　　　　　　　　　　　　　　　　　　　　　　　　　　　20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCCGACACCG GTGACTGAAA　　　　　　　　　　　　　　　　　　　　　　　　　　　　20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTTCAGTCAC CGGTGTCGGA　　　　　　　　　　　　　　　　　　　　　　　　　　　　20

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TAACCGGTAC CTCTAGAAAA TCTAGC                                              26

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TAACCGGTAA GCTTGGGGCT GGGG                                                24

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCGTCTTCAA GAATTCTCA                                                      19

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCATTCTCTA GACACAGGTG                                                     20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GTATATAATG CGGCCGTGGG C                                                   21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCCCACGGCC GCATTATATA C                                                   21

( 2 ) INFORMATION FOR SEQ ID NO:11:

```
( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TAACTCACGT TGTGCATTGT                                                           20

( 2 ) INFORMATION FOR SEQ ID NO:12:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:12:

TCGTCTTCAA GAATTCTCA                                                            19

( 2 ) INFORMATION FOR SEQ ID NO:13:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:13:

ACACCACTCG AGCACGGCAC C                                                         21

( 2 ) INFORMATION FOR SEQ ID NO:14:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:14:

GGTGCCGTGC TCGAGTGGTG A                                                         21
```